United States Patent [19]
Jao et al.

[11] Patent Number: 5,160,744
[45] Date of Patent: Nov. 3, 1992

[54] VERAPMIL THERAPY

[75] Inventors: Frank Jao, San Jose; Patrick S. Wong, Palo Alto; Hoa T. Huynh, Fremont; Kathy McChesney, Cupertino; Pamela K. Wat, Santa Clara, all of Calif.

[73] Assignee: Alza Corporation, Palo Alto, Calif.

[21] Appl. No.: 722,622

[22] Filed: Jun. 27, 1991

[51] Int. Cl.⁵ ............................................ A61K 9/24
[52] U.S. Cl. ..................................... 424/473; 424/497
[58] Field of Search .......................... 424/473, 78, 497

[56] References Cited

U.S. PATENT DOCUMENTS

| | | | |
|---|---|---|---|
| 3,845,770 | 11/1974 | Theeuwes et al. | 128/260 |
| 3,916,899 | 11/1975 | Theeuwes et al. | 128/260 |
| 4,093,709 | 6/1978 | Choi et al. | 424/19 |
| 4,318,400 | 3/1982 | Perry et al. | 128/214 |
| 4,327,725 | 5/1982 | Cortese et al. | 128/260 |
| 4,612,008 | 9/1986 | Wong et al. | 604/892 |
| 4,765,989 | 8/1988 | Wong et al. | 424/473 |
| 4,783,337 | 11/1988 | Wong et al. | 424/468 |
| 4,863,744 | 9/1989 | Urquhart et al. | 424/484 |
| 4,946,685 | 8/1990 | Edgren et al. | 424/472 |
| 4,946,687 | 8/1990 | Ayer et al. | 424/473 |
| 4,948,592 | 8/1990 | Ayer et al. | 424/473 |
| 4,950,486 | 8/1990 | Ayer et al. | 424/473 |
| 4,966,769 | 10/1990 | Guittard et al. | 424/473 |

OTHER PUBLICATIONS

Andreotti, et al, The American Journal of Cardiology, vol. 62, (1988), pp. 635-637.
Ridker, et al, Circulation, vol. 82, (1990), pp. 897-903.
Braunwald, Heart Disease, vol. 2, (1988), pp. 1234-1235.

Primary Examiner—Thurman K. Page
Assistant Examiner—D. Gabrielle Phelan
Attorney, Agent, or Firm—Paul L. Sabatine; Edward L. Mandell; Steven F. Stone

[57] ABSTRACT

A dosage form is disclosed comprising means for delaying the delivery of drug from the dosage form following the administration of the dosage form to a patient in need of drug therapy.

11 Claims, 2 Drawing Sheets

VERAPMIL THERAPY

DISCLOSURE OF TECHNICAL FIELD

This invention pertains to a novel dosage form useful for delayed-drug delivery. More specifically, the invention relates to a dosage form that after administration of the dosage form is followed by a drug-free period, which dosage form at this later time delivers a dose of drug for delayed therapy. The drug is delivered during the drug-delivery period at a controlled rate over time. The invention concerns also a method of delayed-drug therapy by administering a dosage form that delays the onset of drug delivery, and after the drug-free interval delivers a drug for its therapeutic effect.

DISCLOSURE OF BACKGROUND ART

A critical need exists for a dosage form that makes available at a later time a drug to satisfy a therapeutic demand. The demand can arise during a circadian or chronological cycle, or the demand can arise for producing a therapeutic effect a later time, such as during the morning hours. For examples, many patients with myocardial infarction exhibit a clinical incidence of this syndrome that shows a circadian distribution with high frequency in the morning hours between 4:00 a.m. and 9:00 a.m., as reported in *The American Journal of Cardiology*, Vol. 62, pages 635 to 637, 1988; *Circulation*, Vol. 82, pages 897 to 902, 1990; and *Heart Disease*, Vol. 2, pages 1234 to 1235, 1988. Yet, the medical art, previously lacked a dosage form for administering a drug that provides therapy for this application during these critical hours.

There are dosage forms known to the prior art for delivering a drug continuously over time, such as disclosed in U.S. Pat. No. 4,327,725 issued to Cortese and Theeuwes, and in U.S. Pat. Nos. 4,612,008; 4,765,989; and 4,783,337 issued to Wong, Barclay, Deters and Theeuwes. The dosage forms disclosed in these patents comprise a semipermeable wall that surrounds a compartment. The compartment comprises a drug formulation, and in contact with the drug formulation, a displacement member that pushes the drug formulation from the dosage form. These dosage forms operate by imbibing fluid through the semipermeable wall into the compartment, wherein the fluid contacts and motivates the displacement member to consume space and thereby pushes the drug formulation from the dosage form. These dosage forms operate successfully for their intended use, and they can deliver many difficult to deliver drugs for their intended purpose. One limitation, however, associated with these dosage forms, consists in the dosage form immediate delivery of drug to a drug recipient. That is, the dosage forms do not provide for the delayed delivery of a drug to satisfy a future therapeutic need.

It is immediately apparent in the light of the above presentation that a pressing need exists for a dosage form that can delay the delivery of a drug to provide a drug-free interval and then deliver a dose of drug. It will be appreciated by those versed in the dispensing art, that if a novel and unique dosage form is made available for executing a therapeutic program comprising a drug-free interval followed by a drug-delivery interval, such a delayed drug-delivery dosage form would have a practical application, and it would also represent a valuable contribution to the medical arts.

OBJECTS OF THE INVENTION

Accordingly, in view of the above presentation, it is an immediate object of this invention to provide a novel and useful dosage form that represents an unexpected improvement in the dispensing art and substantially overcomes the disadvantages known to the prior art.

Another object of the present invention is to provide a dosage form that can delay the delivery of a beneficial drug.

Another object of the present invention is to provide a dosage form that can delay the delivery of the drug from the dosage form, and then deliver a dose of the drug.

Another object of the present invention is to provide a novel dosage form comprising means for delaying the delivery of drug, followed by means for delivering at a later time a dose of drug.

Another object of the present invention is to provide a novel dosage form comprising means for delaying the delivery of drug for 30 minutes up to 4.5 hours from a dosage form.

Another object of the present invention is to provide a novel dosage form that overcomes the limited functionality of conventional dosage tablets, and which novel dosage form can perform a drug program comprising a drug-free period for a duration as needed, and then to provide a drug-delivery period as needed for a time to achieve a desired therapeutic program.

Another object of the invention is to provide a dosage form comprising in a single dosage form a dosage of drug that is released by the dosage form at least two hours after the dosage form is administered to a drug recipient, and then delivers a drug for a later therapeutic effect.

Another object of the present invention is to provide a novel dosage form manufactured in the form of a drug delivery device comprising means for providing a drug-free interval, and means for then providing a future dose of drug.

Another object of the present invention is to provide a novel dosage form that makes available at a later time a drug for satisfying a need that can arise during a circadian or chronological cycle, or for providing a drug during the morning hours.

Another object of the invention is to provide a therapeutic program comprising an instant dose of drug, followed by a drug-free interval and then a drug-delivery interval.

Other objects, features and advantages of the invention will be more apparent to those versed in the dispensing art from the following specification, taken in conjunction with the drawing figures and the accompanying claims.

BRIEF DESCRIPTION OF THE DRAWINGS

In the drawing figures, which are not drawn to scale, but are set forth to illustrate various embodiments of the invention, the drawing figures are as follows.

Drawing

Drawing

Drawing

Drawing

In the drawing figures and in the specification, like parts in related figures are identified by like numbers. The terms appearing earlier in the specification and in the description of the drawing figures, as well as embodiments thereof, are further described elsewhere in the disclosure.

DETAILED DESCRIPTION OF THE DRAWING FIGURES

Figure 1:
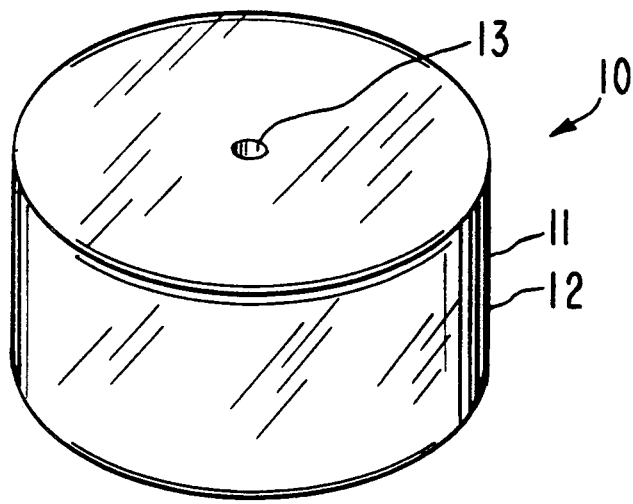
FIG. 1 is a general view of a dosage form provided by the invention, which dosage form is designed and shaped for oral administration, and for a delayed pattern of drug delivery to the gastrointestinal tract.

Turning now to the drawing figures in detail, which drawing figures are examples of dosage forms provided by the invention, and which examples are not to be construed as limiting, one example of a dosage form is seen in drawing FIG. 1. In drawing FIG. 1, a dosage form 10 is seen comprising a body member 11 comprising a wall 12, that surrounds an internal structure not seen in drawing FIG. 1. Dosage form 10 comprises at least one exit port 13 for connecting the exterior with the interior of dosage form 10.

Figure 2:
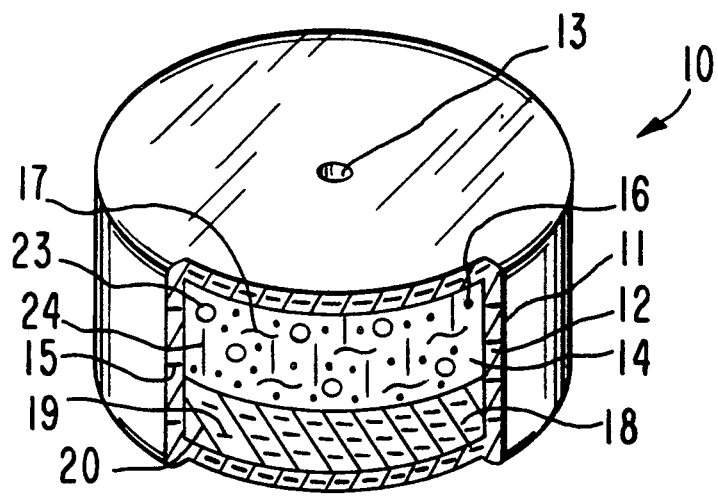
FIG. 2 is an opened view of the dosage form of FIG. 1 for depicting the structure of the dosage form, wherein the wall of the dosage form comprises means for delaying the delivery of drug from the dosage form.

In drawing FIG. 2, dosage form 10 of FIG. 1 is seen in opened section. In drawing FIG. 2, dosage form 10 comprises a body 11, a wall 12 that surrounds and forms internal compartment 14, that communicates through a passageway 13 with the exterior of the dosage form 10. Wall 12 comprises a semipermeable composition and it comprises wall forming means 15 for delaying the delivery of drug 16 from compartment 14. Compartment 14 contains a drug composition 16 comprising drug 16 and polymeric means 17 for delaying the delivery of drug 16. Polymeric means 17 possesses a slow rate of hydration dependent on its high molecular weight and viscosity. The slow rate of hydration of internal polymeric means 17 provides a corresponding slow rate of imbibition of fluid through wall 12, to change the viscosity of means 17 from an essentially non-dispensable phase to a dispensable phase thereby providing a delayed drug delivery followed by a drug-delivery period. Polymeric means 17 operates in conjunction with wall-forming polymeric composition 15 in wall 12. The polymeric composition 15 in wall 12 possesses a slow rate of fluid hydration and this further slows the rate of fluid imbibition by internal polymeric means 17 by restricting fluid to polymeric means 17 and consequently its change in viscosity. The slow rate of hydration in wall 12 generally is from 15 minutes to 3 hours and in a presently preferred manufacture for 15 minutes to 2 hours. The combined operation of internal polymeric means 17 and wall-polymeric composition 15 produces a delayed-drug interval of at least two hours, or more.

Compartment 14 also houses a second or an osmotic composition 18 that is distant from passageway 13 and in contacting relation with the first or drug 16 composition. The second composition 18 contributes a driving force that acts in cooperation with the first or drug 16 composition for delivering the preferred therapeutic amount of drug 16 during the drug delivery interval from dosage form 10. The second composition 18 comprises an optional osmagent 19 represented by dash lines, that is soluble in fluid imbibed into compartment 14, and they exhibit an osmotic pressure gradient across semipermeable wall 12 against an external fluid. The osmagent in another manufacture is blended with an osmopolymer 20, which osmopolymer 20 imbibes fluid into compartment 14 and it exhibits an osmotic pressure gradient across semipermeable wall 12 against an external fluid. The osmopolymer 20 and osmagent 19 are hydrophilic water-loving osmotically effective agents, and they possess osmotic properties such as the ability to imbibe external fluid through semipermeable wall 12. They exhibit an osmotic pressure gradient across the semipermeable wall against the external fluid, and they occupy space for pushing the drug composition by space displacement through exit ports 13. The osmagent 19 is preferably mixed with osmopolymer 20 for imbibing the optimal maximum volume of external fluid into compartment 14. The imbibed fluid is available to optimize the volumetric rate and for expansion of the second composition.

Figure 3:
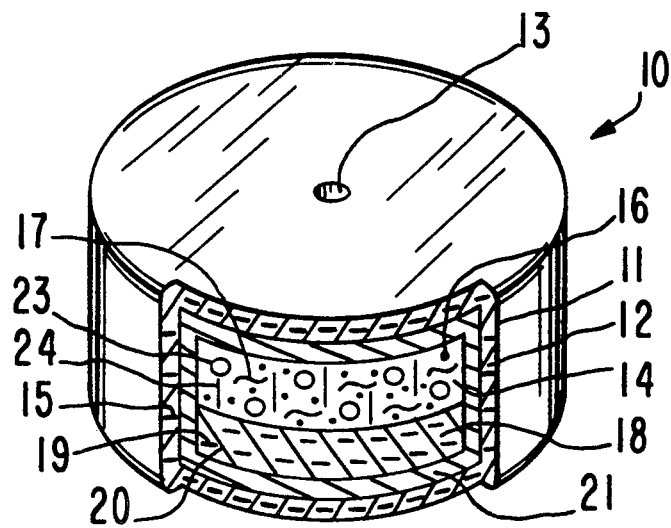
FIG. 3 is an opened view of the dosage form of FIG. 1, for depicting the internal structure of the dosage form, wherein the dosage form comprises an internal coat for delaying drug delivery, which coat surrounds a drug reservoir for delaying the delivery of drug from the reservoir of the dosage form.

Drawing FIG. 3 illustrates another manufacture provide by the invention. Drawing FIG. 3 depicts dosage form 10 comprising body 11, wall 12 comprising chemical means 15 for slowing the rate of fluid imbibition through wall 12 into compartment 14, drug 16 in compartment 14, polymeric viscosity governing means 17 in compartment 14, and second composition 18, which composition 18 comprises at least one of a member selected from the group consisting of osmagent 19 and osmopolymer 20. Dosage form 10, in drawing FIG. 3, comprises a layer 21 that surrounds the drug 16 composition and the osmotic 18 composition. Layer 21 is positioned between the inside of wall 12 and the drug 16 composition and the osmotic 18 composition. Layer 21 comprises a polymer that possesses a resistance to take-up water, and it slows or delays the rate of fluid imbibition into compartment 14. The physics-chemical action of layer 21 thereby contributes to the delayed-delivery of drug 16 from dosage form 10.

Figure 4:
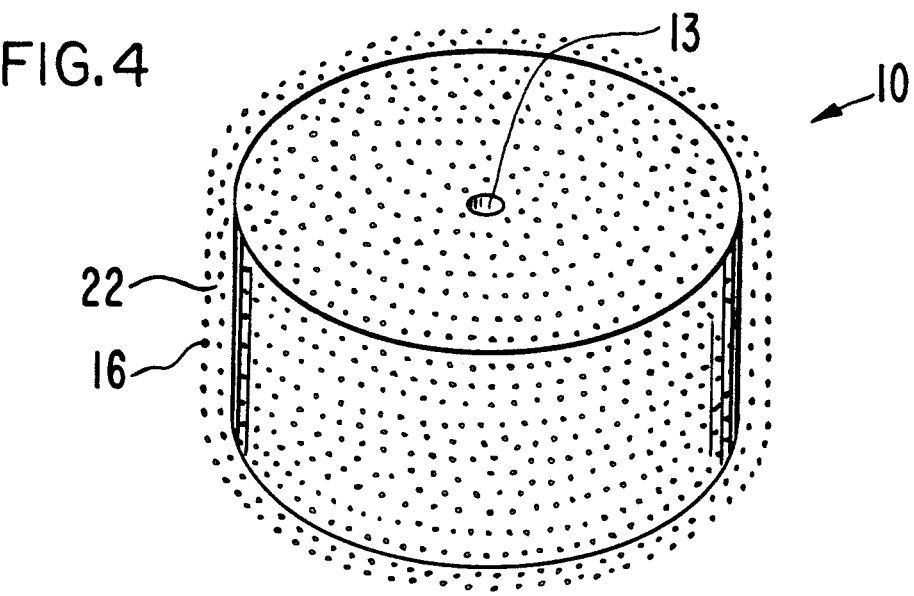
FIG. 4 is an opened view of the dosage form of FIG. 1, comprising external means for delivering an immediate pulsed dose of drug followed by a drug-free interval and then a drug-delivery interval for a therapeutic effect; and, Drawing

Drawing FIG. 4 illustrates another manufacture provided by the present invention. In drawing FIG. 4, dosage form 10 comprises an exterior coat 22 that comprises a dosage unit amount of drug 16 for an initial pulse dose of drug 16 prior to a drug-free interval. The initial pulse is a first dose of drug 16 followed by a drug-free interval, which latter interval is followed by a drug-delivery interval. Exterior coat 22 comprises from about 0.1 to 99.9 weight percent (wt %) of a drug, and from 99.9 to 0.1 wt % of a pharmaceutically acceptable carrier for the drug. The total weight percent of all the coat-forming ingredient is equal to 100 wt %. In a more preferred embodiment the initial pulse dose of drug 16 is from 5 to 75 wt % and from 95 to 25 wt % of the pharmaceutically acceptable carrier. The carrier is a means for coating the drug onto the exterior surface of wall 12. In a fluid environment of use, the carrier releases the drug 16 thereby providing the initial or pulsed dose of drug. The coat 22 releases the initial pulsed dose in from greater than zero time, usually 2.5 minutes up to 1 hour, and in a presently preferred pulsed dose time of from several minutes, more specifically from 5 minutes, up to 30 minutes.

The dosage form 10 of drawing FIGS. 1 through 4 can be used for delivering drugs for their therapeutic benefit. The dosage forms 10 can take a wide variety of shapes, sizes and forms adapted for delivering a drug to the environment of use. For example, the dosage forms include oral, buccal, sublingual, intrauterine, vaginal, anal-rectal and artificial glands dosage forms.

DETAILED DESCRIPTION OF THE INVENTION

In accordance with the practice of this invention it has now been found that a dosage form 10 can be manufactured with a first composition and a different second composition mutually housed in cooperative relationship in the compartment of the dosage form. The dosage form comprises a wall that defines a compartment. The wall comprises a material that does not adversely affect the beneficial drug, osmagent, osmopolymer, and the like. The wall is permeable, that is the wall is permeable to the passage of an external fluid such as water and biological fluids, and it is substantially impermeable to the passage of drugs, osmagents, osmopolymers, and the like. The wall comprises a material that does not adversely affect an animal, or host, or the components comprising the dosage form, and the selectively semipermeable materials used for forming the wall are nonerodible and they are insoluble in fluids. Typical materials for forming the wall are, in one embodiment, cellulose esters, cellulose ethers and cellulose ester-ethers. These cellulosic polymers have a degree of substitution, D.S., on the anhydroglucose unit, from greater than 0 up to 3 inclusive. By degree of substitution is meant the average number of hydroxyl groups originally present on the anhydroglucose unit comprising the cellulose polymer that are replaced by a substituting group. Representative materials include a member selected from the group consisting of cellulose acylate, and cellulose diacylate, cellulose triacylate, cellulose acetate, cellulose diacetate, cellulose triacetate, mono-, di-, and tricellulose alkanylates, mono-, di-, and tricellulose aroylates, and the like. Exemplary polymers include cellulose acetate having a D.S. up to 1 and an acetyl content up to 21%; cellulose acetate having an acetyl content of 32 to 39.8%; cellulose acetate having a D.S. of 1 to 2 and an acetyl content of 21 to 35%; cellulose acetate having a D.S. of 2 to 3 and an acetyl content of 35 to 44.8%, and the like. More specific cellulosic polymers include cellulose propionate having a D.S. of 1.8 and a propyl content of 39.2 to 45% and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7%; cellulose triacylates having a D.S. of 2.9 to 3 , such as cellulose trivalerate, cellulose trilaurate, cellulose tripalmitate, cellulose trisuccinate, and cellulose trioctanoate; cellulose diacylates having a D.S. of 2.2 to 2.6, such as cellulose disuccinate, cellulose dipalmitate, cellulose dioctanoate, cellulose dipentanoate, co-esters of cellulose, such as cellulose acetate butyrate and cellulose acetate propionate.

Additional polymers include ethyl cellulose of various degree of etherification with ethoxy content of from 40 to 55%, acetaldehyde dimethylcellulose acetate, cellulose acetate ethyl carbamate, cellulose acetate methyl carbamate, cellulose acetate diethyl aminoacetate, semipermeable polyamides; semipermeable polyurethanes; semipermeable sulfonated polystyrenes; semipermeable cross-linked selective polymers formed by the coprecipitation of a polyanion and a polycation as disclosed in U.S. Pat. Nos. 3,173,876; 3,276,586; 4,541,005; 3,541,006, and 3,546,142; semipermeable polymers as disclosed by Loeb and Sourirajan in U.S. Pat. No. 3,133,132; semipermeable lightly cross-linked polystyrene derivatives; semipermeable cross-linked poly(sodium styrene sulfonate); semipermeable cross-linked poly(vinylbenzyltrimethyl ammonium chloride); semipermeable polymers exhibiting a fluid permeability of $2.5 \times 10^{-8}$ to $2.5 \times 10^{-4}$(cm$^2$/hr.atm) expressed per atmosphere of hydrostatic or osmotic pressure difference across the semipermeable wall. The polymers are known to the art in U.S. Pat. Nos. 3,845,770; 3,916,899; and 4,160,020; and in *Handbook of Common Plymers*, by Scott, J. R. and Roff, W. J., 1971, published by CRC Press, Cleveland, Ohio.

The polymeric composition 15 present in wall 12 for slowing or for delaying the passage of a fluid, such as water or a biological fluid through wall 12 comprises a polymer exhibiting a 8,500 to 1,000,000 molecular weight, and present in wall 12 in a concentration of 35 wt % to 55 wt %. Polymeric materials operable for the present purpose consists of a member selected from the group consisting of hydroxypropylcellulose, phenylcellulose, benzylcellulose, benzhydrylcellulose, diphenylmethylcellulose and tritylcellulose.

Carrier member 22 used for containing exterior drug 16 in drug-releasing relation, which carrier member 22 is positioned on the exterior surface of wall 12 comprises a member selected from the group consisting of hydroxymethylcellulose, hydroxyethylcellulose, hydroxypropylcellulose, hydroxybutylcellulose, hydroxypentylcellulose, hydroxypropylmethylcellulose, hydroxypropylethylcellulose, hydroxypropylbutylcellulose, and hydroxypropylpentylcellulose. Carrier 22, when present, is from 0.1 mm to 10 mm thick, for providing a dose of drug.

Layer 21 in initial contacting relation with the internal surface of semipermeable wall 12 and in initial contacting relation with drug 16 composition and with push 18 composition, comprises a layer 21, 0.1 mm to 15 mm thick. Layer 21 comprises a member selected from the group consisting essentially of hydroxypropylcellulose, hydroxyphenylcellulose, phenylcellulose, benzylcellulose, benzhydrylcellulose, diphenylmethylcellulose and tritylcellulose. The cellulosic polymer comprising layer 21 can be the same or different than the cellulosic polymer 15 present in wall 12.

In the specification and the accompanying claims, the term "drug 16" includes any physiologically or pharmacologically active substance that produces a local or systemic effect, in animals, including warm-blooded mammals, humans and primates; avians; household, sport and farm animals; laboratory animals; fishes; reptiles and zoo animals. The term "physiologically", as used herein, denote the administration of drug 16 to produce generally normal levels and functions. The term "pharmacologically" denotes generally variations in response to the amount of drug administered to the host. See *Stedman's Medical Dictionary*, 1966, published by Williams and Wilkins, Baltimore, MD. The term "circadian", as used herein, denotes a biological activity that recurs at intervals during a 24 hour period. The phrase "drug formulation", as used herein, means the drug is in the compartment mixed with means for delaying the delivery of drug 16 from dosage form 10. The drug 16 that can be delivered includes inorganic and organic drugs without limitation includes drugs that act on the peripheral nerves, adrenergic receptors, cholinergic receptors, nervous system, skeletal muscles, cardiovascular system, smooth muscles, blood circulatory system, synaptic sites, neuro-effector junctional sites, endocrine system, hormone systems, immunological system, reproductive system, skeletal system, autacoid systems, alimentary and excretory systems, inhibitory of autocoid systems, inhibitory of histamine systems. The active drug that can be delivered for acting on these recipients include anticonvulsants, analgesics, antiparkinsons, anti-inflammatories, calcium antagonists, anesthetics, antimicrobials, antimalarials, antiparasites, antihypertensives, antihistamines, antipyretics, alpha-adrenergic agonist, alpha-blockers, biocides, bactericides, bronchial dilators, beta-adrenergic blocking drugs, contraceptives, cardiovascular drugs, calcium channel inhibitors, depressants, diagnostics, diuretics, electrolytes, hypnotics, hormonals, hyperglycemics, muscle contractants, muscle relaxants, ophthalmics, psychic energizers, parasympathomimetics, sedatives, sympathomimetics, tranquilizers, urinary tract drugs, vaginal drugs, vitamins, nonsteroidal anti-inflammatory drugs, angiotensin converting enzymes, polypeptide drugs, and the like.

Drug 16, that can be dispensed by dosage form 10, is represented by a calcium channel blocker such as nifedipine, isradipine, nilvadipine, verapamil, flunarizine, nimodipine, diltiazem, nicardipine, norverapamil, nitredipine, nisoldipine, felodipine, amlodipine, cinnarizine and fendiline. Drug 16, that also can be dispensed by dosage form 10, is represented by an angiotensin converting enzyme inhibitor selected from the group consisting of angiotensin converting enzyme inhibitors that are essentially-free of sulfur, angiotensin converting enzyme inhibitors containing a sulfhydryl group, angiotensin converting enzyme inhibitors containing a linear sulfide, angiotensin converting enzyme inhibitors containing a cyclic sulfide, and angiotensin converting enzyme inhibitors containing a methylsulfonyl group. Representation of angiotensin converting enzyme inhibitors are more specifically represented by a member selected from the group consisting of ramipril, fosinopril, altiopril, benazepril, libenzapril, alacepril, cilazapril, cilazaprilat, perindopril, zofenopril, enalapril, lisinopril, imidapril, spirapril, rentiapril, captopril, delapril, alindapril, indalapril, and quinapril. The amount of beneficial drug in a dosage form generally is about from 0.05 ng to 1.5 g or more, with individual dosage forms containing, for example, 25 ng, 1 mg, 5 mg, 10 mg, 25 mg, 125 mg, 250 mg, 500 mg, 750 mg, 1.0 g or 1.2 g. The beneficial drugs are known to the art in *Pharmaceutical Sciences*, 14th Ed., edited by Remington, (1979) published by Mack Publishing Co., Easton, Pa; *The Drug, The Nurse, The Patient, Including Current Drug Handbook*, by Falconer, et al.,(1974–1976), published by Saunder Company, Philadelphia, Pa; *Medicinal Chemistry*, 3rd Ed., Vol. 1 and 2, by Burger, published by Wiley-Interscience, N.Y.; and in *Physician's Desk Reference*, 38 Ed., (1984), published by Medical Economics Co., Oradell, N.J.

The drug can be in various forms, such as uncharged molecules, molecular complexes, pharmacologically acceptable salts such as inorganic, organic, hydrochloride, hydrobromide, sulfate, laurate, palmitate, phosphate, nitrite, borate, acetate, maleate, tartrate, oleate and salicylate. For acidic drugs, salts or metals, amines or organic cations; for example, quaternary ammonium can be used. Derivatives of drugs, such as esters, ethers and amides, can be used as represented by, for example, hydroxy, lower alkoxy, lower alkenoxy, diloweralkylamino lower alkoxy (for example, dimethylaminoethoxy), acylamino lower alkoxy (for examples, acetylaminoethoxy), acyloxy lower alkoxy (for example, pivaloyloxyethoxy), aryloxy (for example, phenoxy), aryl lower alkoxy (for example, benzyloxy), amino, lower alkylamino, diloweralkylamino, hydroxyamino, aryllower alkylamino (for example, benzylamino), or substituted aryloxy or substituted aryl-loweralkoxy wherein the substituent is methyl, halo or methoxy.

Figure 5:
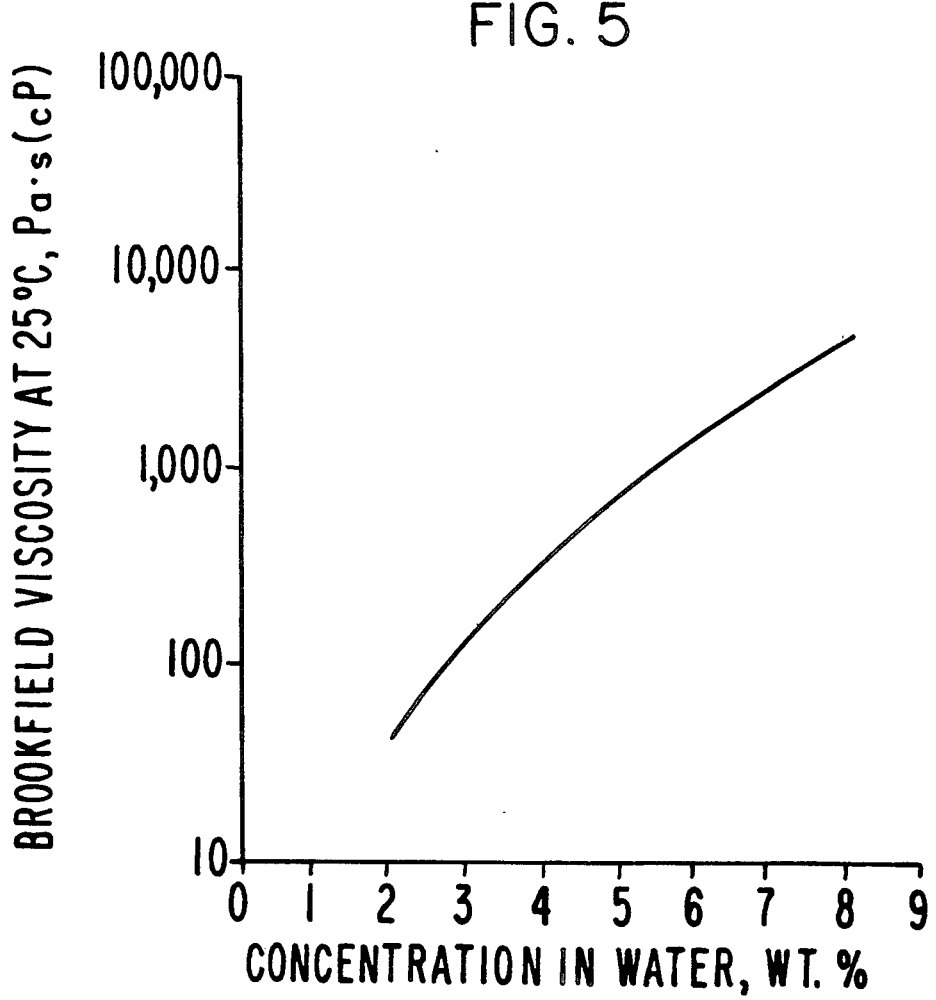
FIG. 5 depicts the change in viscosity for a polymer in response to fluid stress of increasing concentrations.

Polymeric viscosity governing means 17 blended with drug 16, is useful for producing a delay or drug-free interval, according to the mode and the manner of the invention. The polymeric means 17 responds, when fluid stress is applied thereto, to a change from a delayed-drug free state to a dispensable drug delivery state. The change is accompanied by the polymeric means imbibing fluid to increase its viscosity, that is, to change from a non-fluid to a semifluid or viscous dispensable phase. The change can take from 30 minutes up to 4.5 hours, more preferably, from 45 minutes up to 3 hours, thereby producing the drug-free delay period. Representative of a polymeric means operable for the purpose of this invention are polymers comprising a 250,000 to 1,000,000 molecular weight and possess the ability to imbibe fluid for changing over time from a delay to a dispensable state. In a present preferred embodiment, the first composition comprises 20 wt % to 50 wt % of polymeric means 17. The polymers in a 2 wt % to 9 wt % concentration in water exhibit a viscosity at 25° C. of 45 to 10,000 cps (centipoises). More specifically, the presently preferred embodiment comprises polyethylene oxide possessing a 250,000 to 350,000 molecular weight and a 600 to 1,200 viscosity range for a 5% solution at 25° C., cps. The viscosity range for a polymer comprising a 300,000 molecular weight that imbibes an aqueous fluid is seen in accompanying drawing FIG. 5. The polymeric means 17 inside compartment 14 operates in conjunction with polymer 15 in wall 12. Polymer 15 by slowing the fluid flux into compartment 14, limits the volume of aqueous or biological fluid available to polymer 17, thereby concomitantly contributing to the delay interval provided by polymer 17. Polymer 15 and polymer 17 operate together in concert to provide a delay of 2 to 4.5 hours for dosage form 10. Viscosity measurements can be made according to the procedures described in *Chemical Dictionary*, Fifth Ed., by Grant, page 621, (1987), published by McGraw Hill Inc.; *Encyclopedia of Chemistry*, Fourth Edition, pages 822 to 826, (1984), published by Van Nostrand Reinhold Inc.; and in *Pharmaceutical Sciences*, by Remington, 17th Edition, pages 330 to 345, (1985), published by Mack Publishing Co.

The drug composition comprising drug 16 and polymeric means 17 optionally comprises from 0 to 20 wt % of an osmagent. The osmagent are known also as osmotically effective solutes, they are soluble in fluid that enters dosage form 10, and they exhibit an osmotic pressure gradient across semipermeable wall 12 against an exterior fluid. Representative of an osmagent, as seen in drawing FIG. 2, as circle 23, comprise a member selected from the group consisting of magnesium sulfate, magnesium chloride, sodium chloride, lithium chloride, potassium sulfate, sodium sulfate, lithium sulfate and sodium sulfate. The drug composition comprises an optional binder 24, seen in drawing FIG. 2, as a vertical line. The concentration of binder 24 is from 0 wt % to 20 wt %, more preferably from 0 wt % to 10 wt %. Representative of a specific binder for holding the drug composition in core formation, is polyvinylpyrrolidone having a molecular weight of 35,000 to 45,000, usually 38,000 to 40,000. The drug composition comprises 0 wt % to 3.5 wt % of a lubricant, such as magnesium stearate, calcium stearate or stearic acid.

Osmotic composition 18, the second composition comprises an osmopolymer 20. The osmopolymer exhibits fluid absorbing and/or fluid imbibing properties. The osmopolymer comprises a hydrophilic polymer that can interact with water and aqueous fluids and swell or expand to an equilibrium state. The osmopolymer exhibits the ability to retain a significant portion of the imbibed or absorbed fluid. In operation, the drug composition and the osmotic composition cooperate to deliver the drug 16 from dosage form 10. In operation, the osmotic composition absorbs fluid, expands and exerts pressure against the drug composition. The osmopolymers swell or expand to a very high degree, usually to a 2 to 50 fold increase in volume. Representative of osmopolymers consists of a member selected from the group consisting of poly(hydroxyalkyl methacrylate) having a molecular weight of 20,000 to 5,000,000; poly(vinylpyrrolidone) having a molecular weight of about 10,000 to 360,000; poly(vinyl alcohol) having a low acetate content and lightly cross-linked with glyoxal, formaldehyde, glutaraldehyde and having a degree of polymerization from 2,000 to 30,000; poly(ethylene oxide) having a molecular weight from 10,000 to 7,800,000; acidic carboxy polymers known as carboxypolymethylene or as carboxyvinyl polymers, a polymer consisting of acrylic acid lightly cross-linked with polyallylsucrose and sold under the trademark Carbopol ®, acidic carboxy polymer having a molecular weight of 200,000 to 6,000,000, including sodium acidic carboxyvinyl hydrogel and potassium acidic carboxyvinyl hydrogel; Cyanamer ® polyacrylamide; and the like. The representative polymers are known to the art in *Handbook of Common Polymers*, by Scott and Roff, published by the Chemical Company, Cleveland, Ohio; *ACS Symposium Series*, No. 31, by Ratner and Hoffman, pp. 1 to 36, (1976), published by the American Council Society; and in *Recent Advances in Drug Delivery Systems*, by Schacht, pp. 259 to 278, published by Plenum Press, N.Y. The concentration of osmopolymer present in the osmotic composition is from 60 wt % to 85 wt %. The osmotic composition comprises from 2 wt % to 15 wt % of a hydroxypropylalkylcellulose possessing a 9,000 to 25,000 molecular weight and consisting of a member selected from the group consisting of hydroxypropylmethylcellulose, hydroxypropylethylcellulose, hydroxypropylbutylcellulose and hydroxypropylpentylcellulose. The osmotic composition optionally comprises 0.01 to 3.5 wt % of a lubricant, from 0.20 wt % to 2.0 wt % of ferric oxide, and from 15 wt % to 30 wt % of an osmagent. The total weight percent of all ingredients in the osmotic composition is equal to 100 wt %. Osmotically effective osmagents useful for the present purpose include magnesium sulfate, magnesium chloride, sodium chloride, lithium chloride, potassium sulfate, sodium sulfate, sodium carbonate, lithium sulfate, sodium sulfate, and the like. The osmagent is usually present as a particle, powder, granule, or the like. The osmotic pressure in atmospheres, ATM, of the osmagent suitable for the invention will be greater than zero ATM, generally from zero ATM up to 500 ATM, or higher. The osmotic pressure of an osmagent is measured in a commercially available osmometer that measures the vapor pressure difference between pure water and the solution to be analyzed, and according to standard thermodynamic principles the vapor pressure ratio is converted into an osmotic pressure difference. The osmometer used from the present measurements is identified as Model 1001-A Vapor Pressure Osmometer, manufactured by Knauer and distributed by Utopia Instrument Co., Joliet, Ill.

The expression "exit means 13" as used herein comprises means and methods suitable for releasing drug from compartment 14. The expression includes at least one passageway or orifice that passes through wall 12 for communicating with compartment 14. The expression "at least one passageway" includes aperture, orifice, bore, pore, porous element through which drug can migrate, a hollow fiber, capillary tube and the like. The expression includes also a material that erodes or is leached from wall 12 in the fluid environment of use to produce at least one passageway in the dosage form. Representative materials suitable for forming at least one passageway, or a multiplicity of passageways include an erodible polycarbonate, poly(glycolic), or poly(lactic) acid member in the wall, a gelatinous filament, leachable materials such as fluid removable pore forming polysaccharides, salts or oxides, and the like. A passageway or a plurality of passageways can be formed by leaching a material such as sorbitol from the wall to produce a controlled release pore-passageway. The passageway can have any shape, such as round, triangular, elliptical, and the like. The dosage form can be constructed with one or more passageways in spaced apart relation on more than a single surface of a dosage form. Passageways and equipment for forming passageways are disclosed in U.S. Pat. Nos. 3,916,899; 4,063,064; and 4,088,864. Pore-passageways of controlled dimensions formed by leaching are disclosed in U.S. Pat. No. 4,200,098.

The wall 12 of the dosage form 10 and the exterior coat 22 can be formed in one technique using the air suspension procedure. This procedure consists in suspending and tumbling delayed, bilayer compositions in a current of air and a wall forming or outer coat composition, until in either operation the wall or the coat is applied to the delayed bilayer compositions. The air suspension procedure is well-suited for independently forming the wall of the dosage form. The air suspension procedure is described in U.S. Pat. No. 2,799,241; in *J. Am. Pharm. Assoc.*, Vol. 48, pp. 451 to 459, (1959); and, ibid, Vol. 49, pp. 82 to 84, (1960). The osmotic systems can also be coated with the wall forming composition, or the composition with a Wurster ® air suspension coater, using for example, methylene dichloride—methanol cosolvent. The Aeromatic ® air suspension coater can be used also employing a cosolvent. Other coating techniques, such as pan coating, can be used for providing the wall of the dosage form. In the pan coating system the wall 12 forming, or the exterior coat 22 are deposited by successive spraying of the composition on the delayed compositions, accompanied by tumbling in a rotating pan. A pan coater is used because of its availability at commercial scale. An interposed layer, or an external coat can be applied by press coating during the manufacture of the dosage form. Finally, the wall or coated dosage form are dried in a forced air oven at 40°

C. for a week, or in a temperature and humidity controlled oven for 24 hours at 40° C. and 50% relative humidity, to free the dosage form of solvent. Generally, the wall formed by these techniques has a thickness of 2 to 20 mils with a presently preferred thickness of 4 to 10 mils. The exterior coated dose 22 lamina generally will have a thickness of 0.5 to 15 mils, usually 0.5 to 7.5 mils.

Exemplary solvents suitable for manufacturing wall 12 or coat 22 include inert inorganic and organic solvents that do not adversely harm the wall, the lamina and the final dosage system. The solvents broadly include a member selected from the group consisting of an alcohol, ketone, ester, ether, aliphatic hydrocarbon, halogenated solvents, cycloaliphatic solvents, aromatic heterocyclic, aqueous solvents, and mixtures thereof.

The dosage form 10 of the invention is manufactured by standard techniques. For example, in one manufacture, the beneficial drug and other ingredients comprising the first layer facing the exit means are blended and pressed into a solid layer. The layer possesses dimensions that correspond to the internal dimensions of the area the layer is to occupy in the dosage form and it also possesses dimensions corresponding to the second layer for forming a contacting arrangement therewith. The drug and other ingredients can be blended also with a solvent and mixed into a solid or semisolid form by conventional methods, such as ballmilling, calendering, stirring or rollmilling, and then pressed into a preselected shape. Next, a layer of osmopolymer composition is placed in contact with the layer of drug in a like manner. The layering of the drug formulation and the osmopolymer layer can be fabricated by conventional two-layer press techniques. The two contacted layers are first coated with an outer wall 12. The drug composition over outer surface of wall 12 can be applied by press coating, molding, spraying, dipping, and air suspension procedures. The air suspension and air tumbling procedures comprises in suspending and tumbling the pressed, contacting first and second layers in a current of air containing the delayed-forming composition until the first and second layers are surrounded by the wall composition.

In another manufacture, dosage form 10 is manufactured by the wet granulation technique. In the wet granulation technique, the drug and the ingredients comprising the first layer or drug composition, are blended using an organic solvent, such as denature anhydrous ethanol, as the granulation fluid. The ingredients forming the first layer or drug composition are individually passed through a 40 mesh screen and then thoroughly blended in a mixer. Next, other ingredients comprising the first layer can be dissolved in a portion of the granulation fluid, the solvent described above. Then, the latter prepared wet blend is slowly added to the drug blend with continual mixing in the blender. The granulating fluid is added until a wet blend is produced, which wet mass blend is then forced through a 20 mesh screen onto oven trays. The blend is dried for 18 to 24 hours at 24° C. to 35° C. in a forced air oven. The dried granules are then sized with a 20 mesh screen. Next, magnesium stearate is added to the drug screened granulation, is then put into milling jars and mixed on a jar mill for 10 minutes. The composition is pressed into a layer, for example, in a Manesty ® press. The speed of the press is set at 20 rpm and the maximum load set at 2 tons. The first layer is pressed against the composition forming the second layer and the bilayer tablets are fed to the Kilian ® dry Coata press and surrounded with the drug-free coat followed by the exterior wall solvent coating.

Another manufacturing process that can be used for providing the compartment-forming composition comprises blending the powdered ingredients in a fluid bed granulator. After the powdered ingredients are dry blended in the granulator, a granulating fluid, for example, poly(vinylpyrrolidone) in water, is sprayed onto the powders. The coated powders are then dried in the granulator. This process granulates all the ingredients present therein while adding the granulating fluid. After the granules are dried, a lubricant such as stearic acid or magnesium stearate is mixed into the granulation, using a V-blender. The granules are then pressed in the manner described above.

DESCRIPTION OF EXAMPLES OF THE INVENTION

The following examples are merely illustrative of the present invention and they should not be considered as limiting the scope of the invention in any way, as these examples and other equivalents thereof will become more apparent to those versed in the art in the light of the present disclosure, the drawing figures and the accompanying claims.

EXAMPLE 1

A dosage form for the controlled delivery of verapamil, comprising administering a dosage form at bedtime for releasing verapamil to coincide with the early morning rise of blood pressure associated with hypertension and angina, is prepared as follows: first, 600 g of verapamil hydrochloride, 305 g of poly(ethylene oxide) having a molecular weight of 300,000, and 40 g of sodium chloride (powder) were screened through a 40 mesh stainless steel screen and blended with 50 g of polyvinylpyrrolidone, having a molecular weight of 38,000, for 15 minutes in a blender to produce a homogenous mix. The granulating fluid, 350 ml of anhydrous ethyl alcohol, is gradually added into the blended ingredients to produce a wet mass. The wet mass is dried at about 25° C., room temperature, for 16 hours. The dry granules are then passed through a 16 mesh stainless steel screen. Next, 5 g of magnesium stearate is screened through an 80 mesh screen, and the screened granules added to the blended mix and all the ingredients blended in a blender for 2 minutes. This procedure provides the drug composition for providing the drug layer of the reservoir.

The osmotic composition designed for preparing the push layer is made as follows: first, 735 g of polyethylene oxide, having a 7,000,000 molecular weight, 200 g of sodium chloride, 50 g of hydroxypropylmethylcellulose, with a viscosity of 5 cps, and 10 g of red ferric oxide, were screened through a 40 mesh screen and blended for 15 minutes to produce a homogenous mix. Next, 700 ml of anhydrous ethyl alcohol is gradually added to the blended ingredients during blending until a wet granulation is obtained. The wet granulation is then manually screened through the 20 mesh screen and dried at 25° C. for 16 hours. The dry granules are then passed through a 16 mesh screen. Then, 5 g of magnesium stearate, which is prescreened through an 80 mesh screen, is then added to the granules and mixed in a blender for 2 minutes. Next, a drug composition, pressed into a layer, is provided as follows:

| COMPONENTS | WT % | MG/DOSAGE FORM |
|---|---|---|
| DRUG COMPOSITION | | |
| Verapamil HCL | 60.0 | 198.0 |
| Polyox ® N-750 | 30.5 | 100.7 |
| PVP K29-32 | 5.0 | 16.5 |
| NaCl | 4.0 | 13.2 |
| Mg Stearate | 0.5 | 1.7 |
| OSMOTIC COMPOSITION | | |
| Polyox ®-303 | 73.5 | 80.9 |
| NaCl | 20.0 | 22.0 |
| HPMC E-5 | 5.0 | 5.5 |
| $Fe_2O_3$ | 1.0 | 1.1 |
| Mg Stearate | 0.5 | 0.6 |

The abbreviation "Polyox N-750" denotes polyethylene oxide of 300,000 molecular weight, "HPMC E-5" denotes hydroxypropylmethylcellulose of 11,200 molecular weight, "Polyox-303" indicates polyethylene oxide of 7,000,000 molecular weight, and "PVP K29-32" denotes polyvinylpyrrolidone of 38,000 molecular weight.

Next, a wall forming composition comprising 55 wt % cellulose acetate, comprising a 39.8% acetyl content, 40 wt % hydroxypropylcellulose and 5 wt % polyethylene glycol—3350 are dissolved in 80% acetone and 20% methanol was coated around the bilayer core, using a pan coater. A wall weighing 118 mg per dosage form is applied to provide the delayed release dosage form.

Two 30 mil orifices were drilled on the drug composition side of the dosage form. The dosage form exhibited an in vitro 1.5 hours drug-free interval followed by delivering the verapamil drug at a controlled release rate of 20 mg/hour for 8 hours.

EXAMPLE 2

The procedure of Example 1 is followed in this example, with all manufacturing procedures and compositions as previously described, except that, in this example, the osmotic push composition is as follows:

| | OSMOTIC COMPOSITION | |
|---|---|---|
| COMPONENTS | WT % | MG/DOSAGE FORM |
| Polyox ®-303 | 73.5 | 147.0 |
| NaCl | 20.0 | 40.0 |
| HPMC E-5 | 5.0 | 10.0 |
| $Fe_2O_3$ | 1.0 | 2.0 |
| Mg Stearate | 0.5 | 1.0 |

Three 30 mil orifices were drilled on the drug side of each dosage form. The dosage form exhibited a 1 hour drug-free interval followed by delivering 40 mg/hour of verapamil over 5 hours.

EXAMPLE 3

An osmotic dosage form for the controlled and continuous release of a calcium channel blocker drug as exemplified by verapamil after a programmed delay of about 2 hours, was made as follows: first, 5,400 g of verapamil hydrochloride, 2,745 g of poly(ethylene oxide) of 300,000 molecular weight, 225 g of polyvinylpyrrolidone of 38,500 molecular weight and 360 g of sodium chloride were passed through a 16 mesh screen. Next, the screened excipients were introduced into the fluid bed granulator for 30 minutes and preheated to 35° C. A granulation solution consisting of 225 g of polyvinylpyrrolidone of 40,000 molecular weight dissolved in 2,588 g of distilled water was sprayed onto the fluidized powders in the granulator. Then, 45 g of magnesium stearate, which is prescreened through an 80 mesh screen, were added to the granules in a mixer and the ingredients blended for 3 minutes.

An osmotic push composition was prepared in a similar manner. The composition comprised 117,600 g of polyethylene oxide with a 7,500,000 molecular weight, 32,000 g of sodium chloride, 3,200 g of hydroxypropylmethylcellulose of 11,200 molecular weight, and 1,600 g of ferric oxide were screened through a 17 mesh screen. Next, the screened ingredients were introduced into a fluid bed granulator for 30 minutes preheated to 35° C. A granulating fluid consisting of 4,800 g of hydroxypropylmethylcellulose, of 5 cps viscosity dissolved into 55,200 g of distilled water, was sprayed onto the fluidized ingredients.

Next, a bilayer core comprising a drug composition and a push composition was prepared in a Manesty ® Tablet Press. The bilayer cores were surrounded with a cellulose acetate, hydroxypropylcellulose wall and an orifice drilled through the wall is described in Example 1. The dosage form after a 2 hour drug delay period delivers 21 mg/hour of drug over a prolonged period of time.

EXAMPLE 4

The procedures described in the above examples are repeated in this example, with all the conditions as previously set forth, except that in this example, the drug is a calcium channel blocking drug selected from the group consisting of nifedipine, isradipine, nilvadipine, flunarizine, nimodipine, diltiazem, nicardipine, nitredipine, nisoldipine, felodipine, amlodipine, cinnarizine and fendiline.

EXAMPLE 5

The procedure described in the above examples is repeated in this example, with all the conditions as previously set forth, except that, in this example, the drug is an angiotensin converting enzyme inhibitor selected from the group consisting of alacipril, benazepril, cialzapril, captopril, delapril, enalapril, fosinopril, lisinopril, moveltipril, perindopril, quinapril, ramipril, spirapril, and zofenopril.

EXAMPLE 6

The dosage form prepared according to the above examples, wherein the dosage form is an osmotic delivery device comprising a caplet shape for easy oral drug administration.

EXAMPLE 7

In this example, the rate of hydration of (1) a wall composition comprising 60 wt % cellulose acetate consisting of 39.8% acetyl content, 35 wt % polyvinylpyrrolidone of 38,000 molecular weight and 5 wt % polyethylene glycol 3350 is compared with the rate of hydration of (2) a wall composition comprising 60 wt % cellulose acetate comprising a 39.8% acetyl content, 35 wt % hydroxypropylcellulose of 38,000 molecular weight and 5 wt % polyethylene glycol 3350. The composition (1) comprising polyvinylpyrrolidone hydrates quickly and lets fluid pass into the dosage form, while composition (2) comprising hydroxypropylcellulose hydrates very slowly and substantially delays the passage of fluid into the dosage form for 2 hours. The composition (2) operates with synergetic effect with the drug composition comprising a polymer of 250,000 to 350,000 molecular weight. Polymers of lower molecular weight are substantially devoid of delay, which the polymer used by this invention exhibits a long delay prior to converting to a drug delivery phase.

EXAMPLE 8

In this example, the above procedures are followed, with the added manufacture a hydroxypropylcellulose is interposed between the inside of the semipermeable wall and around the first or drug composition and the second or push composition. The interposed layer is about 6 mm thick and it slows or delays the rate of fluid imbibition into the first and second composition. The layer is applied as a dry composition by press coating the layer in the interposed position.

EXAMPLE 9

The procedures of the above examples are repeated in this example, with the added embodiment comprising the wall, which is coated on its outer surface with an instant dose of verapamil hydrochloride.

METHOD OF PRACTICING THE INVENTION

A presently preferred embodiment of the invention pertains to a method for delivering a drug to a patient during a circadian cycle comprising an active phase and a less active phase, wherein the method comprises: (A) orally admitting into the patient a dosage form comprising means for delivering a drug during the active phase and means for providing a drug-free interval during the less active phase. The method comprises: (B) admitting into the patient a dosage form comprising: (1) a wall that surrounds and forms an internal compartment, said wall comprising a composition for slowing the fluid flux through the wall; (2) a drug composition in the compartment, said composition comprising means for delaying the delivery of drug from the dosage form; (3) a push composition in the compartment for pushing the drug composition from the dosage form; (4) an orifice in the dosage form for delivering the drug from the dosage form; (B) imbibing fluid through the wall at a rate determined by the osmotic pressure gradient across the wall, thereby causing the drug composition to slowly form a dispensable composition and the push composition to absorb fluid and push the dispensable drug composition from the dosage form; and, (C) delivering the drug after a drug-free interval to the patient. The invention provides also an instant dose of drug by delivering a drug from an external instant release drug coat. In this delivery pattern, the instant release is followed by a drug-free interval. The method of the invention for the treatment of hypertension and angina provides a drug-free interval when a patient is less active, that is, at rest or when asleep and the invention provides drug during the rising or waking hours mainly during the time when activity reaches a maximum during the daytime hours.

The novel osmotic dosage form of this invention uses dual means for the attainment of precise release rate of drugs that are difficult to deliver in the environment of use, while simultaneously maintaining the integrity and the character of the system. While there has been described and pointed out features and advantages of the invention, as applied to the presently preferred embodiments, those skilled in the dispensing art will appreciate that various modifications, changes, additions, and omissions in the system illustrated and described can be made without departing from the spirit of the invention.

We claim:
1. A dosage form for the delayed-delivery of a drug, wherein the dosage form comprises:
(a) a first composition comprising 0.05 nanograms to 1.5 grams of the drug verapamil and 20 wt % to 50 wt % of a poly(ethylene oxide) present in the first composition, said poly(ethylene oxide) comprising means for changing from a nondispensable viscosity to a dispensable viscosity when contacted by fluid that enters the dosage form;
(B) a second composition comprising a polymeric composition that imbibes fluid and expands, whereby the second composition pushes the first composition from the dosage form;
(C) a wall that surrounds the first and second compositions, said wall permeable to the passage of fluid present in the environment of use and comprises 35 wt % to 55 wt % of a polymeric composition that hydrates slowly when contacted by fluid that enters the wall;
(D) at least one exit means in the wall for delivering the drug from the dosage form; and, wherein the dosage form is characterized by:
(E) a delayed-drug interval for delivering verapamil up to 4.5 hours provided by (A), (B) and (C) operating in combination as a unit to provide the delayed-drug interval.

2. The dosage form for the delayed-delivery of a drug according to claim 1, wherein the drug verapamil is replaced by a different drug selected from the group consisting of a calcium channel blocker and its pharmaceutically acceptable derivatives.

3. The dosage form for the delayed-delivery of a drug according to claim 1, wherein the drug verapamil is replaced by a member selected from the group consisting of nifedipine, nilvadipine, flunarizine, nimodipine, diltiazem, nicardipine, nitredipine, nisoldipine, felodipine, amlodipine, cinnarizine, and fendiline.

4. The dosage form for the delayed-delivery of a drug according to claim 1, wherein the drug verapamil is a member selected from the group consisting of verapamil and its pharmaceutically acceptable salts.

5. The dosage form for the delayed-delivery of a drug according to claim 1, wherein the drug verapamil is replaced by a member selected from the group consisting of ramipril, fosinopril, altiopril, benazepril, libenzapril, alacepril, cialzapril, cilazaprilat, perindopril, zofenopril, enalapril, lisinopril, imidapril, spriapril, rentiapril, captopril, delapril, olindapril, indalapril and quinapril.

6. The dosage form for administering the drug according to claim 1, wherein the orifice is a pore-orifice.

7. A method for administering the drug verapamil to the gastrointestinal tract of a patient in need of verapamil therapy, which method comprises:
(A) admitting a dosage form into the gastrointestinal tract of the patient, said dosage form comprising:
(1) a wall that surrounds and defines the compartment, said wall comprising 35 wt % to 55 wt % of a hydroxypropylcellulose and a member selected from the group consisting of cellulose acetate, cellulose diacetate, and cellulose triacetate;
(2) a drug composition in the compartment, said compartment comprising a therapeutically effective dose of 0.05 nanograms to 1.5 grams of the verapamil drug and 20 wt % to 50 wt % of a poly(ethylene oxide);

(3) a push composition in the compartment that imbibes fluid into the compartment, expands and pushes the drug composition from the dosage form, said push composition comprising a poly(ethylene oxide) which is different than the poly(ethylene oxide) in the drug composition; and (4) a passageway in the dosage form for delivering the drug composition from the dosage form; and, wherein the dosage form in the gastrointestinal tract;

(B) changes from a delayed drug-free state over 30 minutes to 4.5 hours to a dispensable drug-delivery state; and, (C) administering the drug verapamil to the gastrointestinal tract of the patient by the push composition displacing the drug from the dosage form.

8. The method for administering the drug verapamil to the gastrointestinal tract of a patient according to claim 7, wherein an instant dose of verapamil is administered from an external coat in contact with the wall.

9. The method for administering the drug verapamil to the gastrointestinal tract of a patient according to claim 7, wherein the dosage form delivers verapamil after a 2 hour drug-free interval.

10. The method for administering the drug verapamil to the gastrointestinal tract of a patient according to claim 7, wherein the dosage form is administered at bedtime.

11. The method for administering the drug verapamil to the gastrointestinal tract of a patient according to claim 7, wherein the dosage form administers verapamil during the night hours.

* * * * *

UNITED STATES PATENT AND TRADEMARK OFFICE
CERTIFICATE OF CORRECTION

PATENT NO. : 5,160,744

DATED : November 3, 1992

INVENTOR(S) : Frank Jao, Patrick S. L. Wong, Hoa T. Huynh, Kathy McChesney, Pamela K. Wat It is certified that error appears in the above-identified patent and that said Letters Patent is hereby corrected as shown below:

Item [54] on Title page, "VERAPMIL THERAPY" should read --VERAPAMIL THERAPY--, Column 1, line 1, "VERAPHIL THERAPY" should read --VERAPAMIL THERAPY--.

Signed and Sealed this

Ninth Day of November, 1993

*Attest:*

BRUCE LEHMAN

*Attesting Officer*       Commissioner of Patents and Trademarks